US010260091B2

United States Patent
Brettschneider et al.

(10) Patent No.: US 10,260,091 B2
(45) Date of Patent: Apr. 16, 2019

(54) ANALYSIS UNIT FOR PERFORMING A POLYMERASE CHAIN REACTION, METHOD FOR OPERATING SUCH AN ANALYSIS UNIT, AND METHOD FOR PRODUCING SUCH AN ANALYSIS UNIT

(71) Applicant: Robert Bosch GmbH, Stuttgart (DE)

(72) Inventors: Thomas Brettschneider, Leonberg (DE); Jochen Hoffmann, Renningen (DE)

(73) Assignee: Robert Bosch GmbH, Stuttgart (DE)

( * ) Notice: Subject to any disclaimer, the term of this patent is extended or adjusted under 35 U.S.C. 154(b) by 363 days.

(21) Appl. No.: 15/025,077

(22) PCT Filed: Sep. 19, 2014

(86) PCT No.: PCT/EP2014/069963
§ 371 (c)(1),
(2) Date: Mar. 25, 2016

(87) PCT Pub. No.: WO2015/044040
PCT Pub. Date: Apr. 2, 2015

(65) Prior Publication Data
US 2016/0265026 A1    Sep. 15, 2016

(30) Foreign Application Priority Data

Sep. 27, 2013 (DE) .................. 10 2013 219 502

(51) Int. Cl.
*C12M 1/34* (2006.01)
*C12Q 1/686* (2018.01)
*B01L 3/00* (2006.01)

(52) U.S. Cl.
CPC .......... *C12Q 1/686* (2013.01); *B01L 3/50273* (2013.01); *B01L 3/502707* (2013.01);
(Continued)

(58) Field of Classification Search
CPC ......... B01L 3/05027; B01L 2400/0481; B01L 2400/0487; B01L 2400/0489; B01L 2400/0638
See application file for complete search history.

(56) References Cited

U.S. PATENT DOCUMENTS 5,851,492 A * 12/1998 Blattner ................ B01L 3/5085
422/569
6,309,889 B1 * 10/2001 Cutler .................. B01J 19/0046
422/500

(Continued)

FOREIGN PATENT DOCUMENTS

CN          1950520 A     4/2007
CN        101171346 A     4/2008
(Continued)

OTHER PUBLICATIONS

International Search Report corresponding to PCT Application No. PCT/EP2014/069963, dated Mar. 9, 2015 (German and English language document) (5 pages).

*Primary Examiner* — William H. Beisner
(74) *Attorney, Agent, or Firm* — Maginot, Moore & Beck LLP

(57) ABSTRACT

An analysis unit for performing a polymerase chain reaction includes a cover element, a bottom element, at least one fluid channel, at least one pressure channel, and a film. The bottom element has at least one bottom hollow that defines a fluid-accommodating surface and an arrangement of microcavities, and that faces toward the cover element. The fluid channel is formed between the cover element and the bottom element in order to conduct a fluid onto the fluid-accommodating surface. The pressure channel is formed in the cover element in order to conduct a pressure into a region of the fluid-accommodating surface. The film is positioned between the cover element and the bottom element in a (Continued)

region of the bottom hollow, and is configured to deform in response to the pressure conducted through the pressure channel such that the fluid is moved through the fluid-accommodating surface into the arrangement of microcavities.

13 Claims, 5 Drawing Sheets

(52) U.S. Cl.
CPC ... *B01L 3/502715* (2013.01); *B01L 3/502746* (2013.01); *B01L 2200/0642* (2013.01); *B01L 2300/041* (2013.01); *B01L 2300/0848* (2013.01); *B01L 2300/0861* (2013.01); *B01L 2300/0887* (2013.01); *B01L 2300/123* (2013.01); *B01L 2300/14* (2013.01); *B01L 2400/0481* (2013.01)

(56) References Cited

U.S. PATENT DOCUMENTS

| | | | |
|---|---|---|---|
| 7,431,884 B2* | 10/2008 | Ryan | B01F 11/0071 422/561 |
| 8,222,023 B2* | 7/2012 | Battrell | B01F 11/0071 435/286.5 |
| 2003/0233827 A1 | 12/2003 | Kuo et al. | |
| 2005/0180891 A1 | 8/2005 | Webster et al. | |
| 2006/0275852 A1 | 12/2006 | Montagu et al. | |
| 2008/0241890 A1* | 10/2008 | Gumbrecht | C12Q 1/686 435/91.2 |
| 2009/0060791 A1 | 3/2009 | Hagiwara et al. | |
| 2009/0202391 A1 | 8/2009 | Hagiwara et al. | |

FOREIGN PATENT DOCUMENTS

| | | |
|---|---|---|
| CN | 101262948 A | 9/2008 |
| CN | 101389406 A | 3/2009 |
| CN | 101663585 A | 3/2010 |
| CN | 102665915 A | 9/2012 |
| JP | 2010151717 A | 7/2010 |

* cited by examiner

ANALYSIS UNIT FOR PERFORMING A POLYMERASE CHAIN REACTION, METHOD FOR OPERATING SUCH AN ANALYSIS UNIT, AND METHOD FOR PRODUCING SUCH AN ANALYSIS UNIT

This application is a 35 U.S.C. § 371 National Stage Application of PCT/EP2014/069963, filed on Sep. 19, 2014, which claims the benefit of priority to Serial No. DE 10 2013 219 502.8, filed on Sep. 27, 2013 in Germany, the disclosures of which are incorporated herein by reference in their entirety.

BACKGROUND

The present disclosure relates to an analysis unit for performing a polymerase chain reaction, a method for operating such an analysis unit, and a method for producing such an analysis unit.

The digital polymerase chain reaction permits the detection of individual DNA sequences in a cavity array. For this purpose, n DNA molecules are randomly distributed together with a biochemical amplification system (polymerase chain reaction (PCR)) on m microcavities of a chip, where n is normally smaller than m. In each cavity, in which one DNA molecule was initially present, millions of identical copies of the DNA molecule are generated and, at the same time, a detectable signal is generated. By counting the signals, it is thus possible, after the polymerase chain reaction, to distinguish "digitally" between empty cavities (=0) and cavities with a DNA molecule (=1).

In commercially available systems for digital polymerase chain reactions, a biological sample is initially disrupted, and the DNA is then purified and extracted.

Microfluidic diagnostic systems such as lab-on-a-chip (LOC) systems permit the miniaturized and integrated performance of complex work steps such as fully automated sample preparation. In such lab-on-a-chip systems, the sample material to be tested can first of all be amplified by means of polymerase chain reaction and then analyzed on a microarray. The link between both operations and the multiple steps of the process result in a protracted processing time and complex processing. By contrast, the digital polymerase chain reaction makes it possible for DNA molecules to be specifically amplified and quantified in one step.

SUMMARY

Against this background, the present disclosure proposes an analysis unit for performing a polymerase chain reaction, a method for operating such an analysis unit, and a method for producing such an analysis unit. Advantageous refinements are set forth in the claims and in the description below.

An analysis unit for performing a polymerase chain reaction is proposed, wherein the analysis unit has the following features:

a cover element;

a bottom element with at least one bottom hollow, wherein the bottom hollow has a fluid-receiving surface and an arrangement of microcavities, wherein the bottom hollow is arranged lying opposite the cover element;

at least one fluid channel, which is formed between the cover element and the bottom element in order to convey a fluid onto the fluid-receiving surface of the bottom hollow;

at least one pressure channel, which is formed in the cover element in order to convey a pressure into an area of the fluid-receiving surface; and a film, which is arranged between the cover element and the bottom element in the area of the bottom hollow, wherein the film is designed to be deformed by pressure, when the pressure is conveyed into the area of the fluid-receiving surface, in such a way that the fluid is moved from the fluid-receiving surface into the arrangement of microcavities.

A cover element and a bottom element can each be understood as a layer which is produced, for example, from a plastic, in particular from a polymer. A bottom hollow can be understood, for example, as a depression in the bottom element. A fluid-receiving surface can be understood as a surface of the bottom hollow onto which a fluid can be applied. A fluid can be understood as a liquid with biochemical material, for example nucleic acids. A microcavity can be understood as a depression made in the bottom hollow and designed to take up the fluid. For example, the fluid can be introduced into the microcavity in order to perform a polymerase chain reaction. A film can be understood as a planar flexible element, for example a layer of plastic. The film can be impermeable to fluid, for example.

The present approach is based on the recognition that it is possible for an array of microcavities for performing analyses by means of polymerase chain reaction to be integrated in a lab-on-a-chip system. For example, preparation of a sample solution that is to be analyzed can also take place in the lab-on-a-chip system. Advantageously, a membrane of the lab-on-a-chip system can be used to fill the sample solution into the microcavities after preparation. For this purpose, the membrane can be deflected by means of a pressure, in such a way that the sample solution is forced into the microcavities.

By virtue of the fact that the microarray can be filled automatically and in a controlled manner, a process sequence can be greatly accelerated and simplified by comparison with a manual transfer of the sample solution. Moreover, operating errors can thus be excluded, and costs expended on specially trained personnel can be saved. Finally, the proposed approach affords the advantage of a reduced risk of contamination.

According to one embodiment of the present approach, the pressure channel can be formed as a through-opening in the cover element. Here, the bottom hollow can be arranged in such a way that the fluid-receiving surface lies opposite the through-opening, and the arrangement of microcavities is laterally offset with respect to the through-opening. In this way, an efficient control of the film can be achieved with little outlay in terms of costs.

According to one embodiment of the present approach, the film can be secured releasably on the cover element at least in the area of the fluid-receiving surface and/or in the area of the arrangement of microcavities. This has the effect that, when the pressure is applied at the through-opening, the film bulges continuously away from the fluid-receiving surface in the direction of the microcavities. This affords the advantage of very reliable filling of the microcavities.

The film can moreover be designed to be deformed by the pressure in such a way that the arrangement of microcavities is closed in a fluid-tight manner. Since the microcavities are filled and closed in a fluid-tight manner in one step, early evaporation of the fluid can be prevented.

Moreover, a separation element can be formed between the arrangement of microcavities and the fluid-receiving surface, in order to prevent a movement of the fluid from the fluid-receiving surface into the arrangement of microcavities before the pressure has been conveyed into the area of the fluid-receiving surface. A separation element can be understood, for example, as a groove formed in the bottom hollow and extending transversely with respect to a direction of movement of the fluid, or as a strip of a hydrophobic material applied to the bottom hollow. Such a separation element, which is easy to produce, allows the fluid to be introduced into the analysis unit quickly and in a controlled manner.

According to a further embodiment of the present approach, the fluid-receiving surface can be at least partially covered with a compressible fiber layer for taking up and/or releasing the fluid. A fiber layer can be understood as a layer of a liquid-absorbing material, for example a nonwoven. For example, the fiber layer can be formed to absorb a predetermined maximum volume of the fluid. Thus, not only can an accidental movement of the fluid from the fluid-receiving surface into the arrangement of microcavities be prevented, it is also possible for an amount of the fluid to be measured off.

Furthermore, the bottom element can have a predetermined maximum thickness in the area of the arrangement of microcavities. For example, a small maximum thickness affords the advantage that the temperature of the microcavities can be quickly and efficiently regulated in order to perform a temperature-controlled polymerase chain reaction. Moreover, light absorption by the bottom element in the area of the microcavities can be reduced. This may be advantageous in particular when using optical methods to analyze the fluid.

The film, at least in the area of the arrangement of microcavities, can have an insulation layer and/or can be designed as a multi-layer composite in order to reduce a vapor permeability of the film. In this way, diffusion losses can be effectively counteracted and a high degree of reliability of the analysis unit can be ensured.

According to a further embodiment, the insulation layer can be formed on a side of the film facing toward the cover element. In particular, the insulation layer can in this case be formed from paraffin. Since the paraffin has a solid state and, for example, changes to a liquid state only when the analysis unit is heated, the insulation layer can be applied very easily to the film during the production of the analysis unit.

According to a further embodiment of the present approach, a fluid container can be formed as a further bottom hollow in the bottom element. In this case, at least one further pressure channel can be formed in the cover element in order to convey a pressure into the fluid container. Moreover, at least one connection channel can be formed in the cover element in order to couple the fluid container and the pressure channel fluidically. The fluid container can be designed to convey the pressure through the connection channel and the pressure channel into the area of the fluid-receiving surface. A fluid container can be understood, for example, as a liquid-filled depression in the bottom element. The liquid can be water in particular. Since the water over the deflected film serves as a kind of diffusion barrier, an evaporation of a liquid located in the microcavities can be reduced. Moreover, this embodiment affords the advantage of simplified handling of the analysis unit, since no liquid has to be delivered from outside.

According to a further embodiment, the film can also be arranged in the area of the fluid container in order to close the fluid container in a fluid-tight manner. In this case, the pressure can act on the liquid through a deflection of the film.

According to a further embodiment of the present approach, the analysis unit can also have a means designed to introduce a pressure into the pressure channel and/or the further pressure channel. A means can be understood, for example, as a pump which is designed to pump a fluid into the pressure channel and/or the further pressure channel. The fluid can in particular be a liquid. A pressure that is needed to deflect the film can be reliably made available by the means. Use of the liquid affords the additional advantage of reducing the vapor permeability of the film, insofar as the film is covered by the liquid in the area of the microcavities.

The present approach moreover makes available a method for operating an analysis unit according to one of the above-described embodiments, which method comprises the following steps:

applying a fluid to the fluid-receiving surface; and introducing a pressure into the pressure channel in order to move the fluid from the fluid-receiving surface into the arrangement of microcavities.

Finally, the present approach makes available a method for producing an analysis unit according to one of the above-described embodiments, which method comprises the following steps:

making available a bottom element with at least one bottom hollow which has a fluid-receiving surface and an arrangement of microcavities, a cover element with at least one pressure channel which is designed to convey a pressure into the area of the fluid-receiving surface, and a film which is designed to be deformed by pressure, when the pressure is conveyed into the area of the fluid-receiving surface, in such a way that a fluid is moved from the fluid-receiving surface into the arrangement of microcavities;

joining together the cover element, the bottom element and the film, wherein the joining together takes place in such a way that the bottom hollow lies opposite the cover element and the film is arranged between the cover element and the bottom element in the area of the bottom hollow; and forming at least one fluid channel between the cover element and the bottom element, in order to convey the fluid onto the fluid-receiving surface of the bottom hollow.

BRIEF DESCRIPTION OF THE DRAWINGS

The disclosure is explained in more detail below on the basis of examples and with reference to the attached drawings, in which.

DETAILED DESCRIPTION

In the following description of expedient illustrative embodiments of the present disclosure, elements that are shown in the different figures and have a similar action are labeled by identical or similar reference signs, in which case a repeated description of these elements is omitted.

Figure 1A:
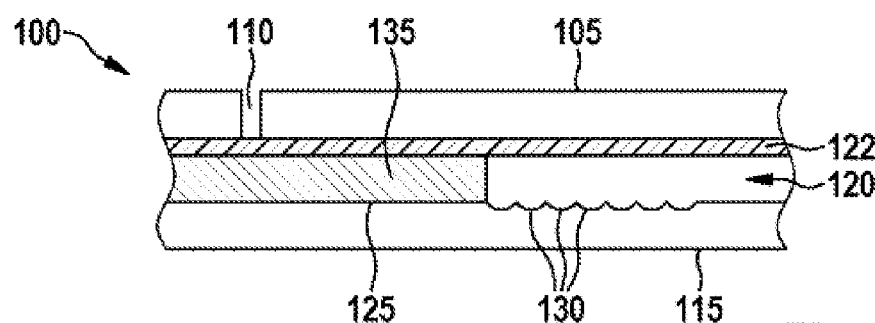
FIGS. 1a, 1b and 1c show cross-sectional views of an analysis unit according to an illustrative embodiment of the present disclosure.
Figure 1B:
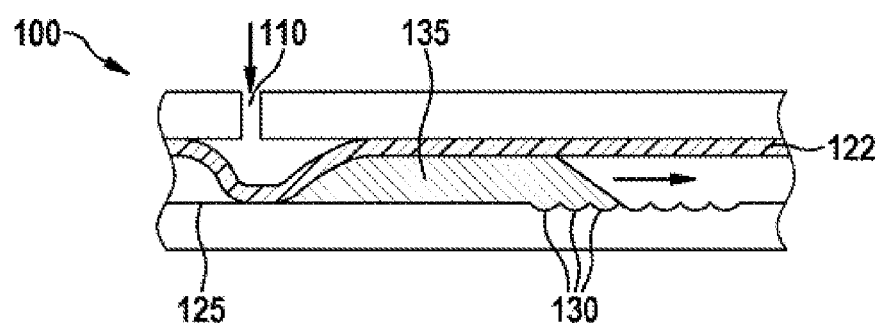
Figure 1C:
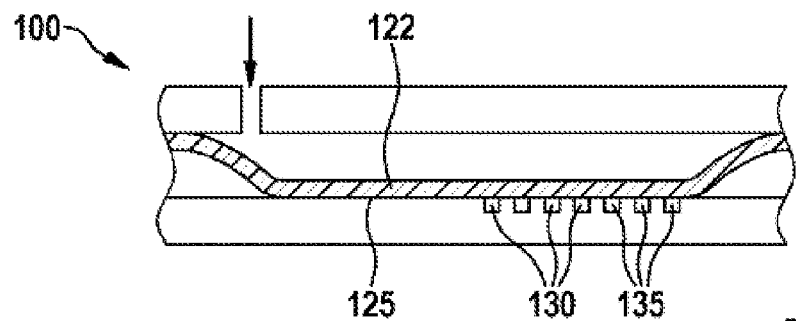

FIGS. 1a, 1b and 1c show cross-sectional views of an analysis unit 100 according to an illustrative embodiment of the present disclosure. The analysis unit 100 comprises a cover element 105 with a pressure channel 110, a bottom element 115 with a bottom hollow 120, and a film 122. According to this illustrative embodiment, the pressure channel 110 is formed as a through-opening in the cover element 105. The bottom hollow 120 has a fluid-receiving surface 125 and an arrangement of microcavities 130. The film 122 is arranged between the cover element 105 and the bottom element 150 in the area of the bottom hollow 120. The bottom hollow 120 is arranged in such a way that the fluid-receiving surface 125 lies opposite the pressure channel 110 and the microcavities 130 are offset laterally with respect to the pressure channel 110. A fluid 135 is situated on the fluid-receiving surface 125, the volume of said fluid 135 filling a cavity between the fluid-receiving surface 125 and the film 122. The fluid 135 moreover extends as far as an edge area of the fluid-receiving surface 125 adjoining the arrangement of microcavities 130. In order to convey the fluid 135 onto the fluid-receiving surface 125, a channel (not visible) is formed between the cover element 105 and the bottom element 115.

When a pressure is applied to the pressure channel 110, the film 122 is designed to be deformed by the pressure in such a way that the fluid 135 is moved from the fluid-receiving surface 125 into the microcavities 130.

FIG. 1a shows the analysis unit 100 in a non-activated state.

FIG. 1b shows the analysis unit 100 when the pressure is applied to the pressure channel 110. A direction of the pressure is indicated by an arrow. The film 122 is bulged outward by the pressure, in such a way that it bears on the fluid-receiving surface 125. The film 122 initially bears on the fluid-receiving surface 125 only in the area of the through-opening 110. This has the effect that the fluid 135 is forced from the fluid-receiving surface 125 in the direction of the microcavities 130, such that some of the microcavities 130 are filled with the fluid 135. A direction of movement of the fluid 135 is indicated by a further arrow.

The film 122 is bulged outward continuously in the direction of the microcavities 130 by the pressure until it bears with its entire surface area on the fluid-receiving surface 125 and the microcavities 130, as shown in FIG. 1c.

FIG. 1c shows the analysis unit 100 in a fully activated state. Here, all of the microcavities 130 are filled with the fluid 135 and covered by the film 122.

Figure 2:
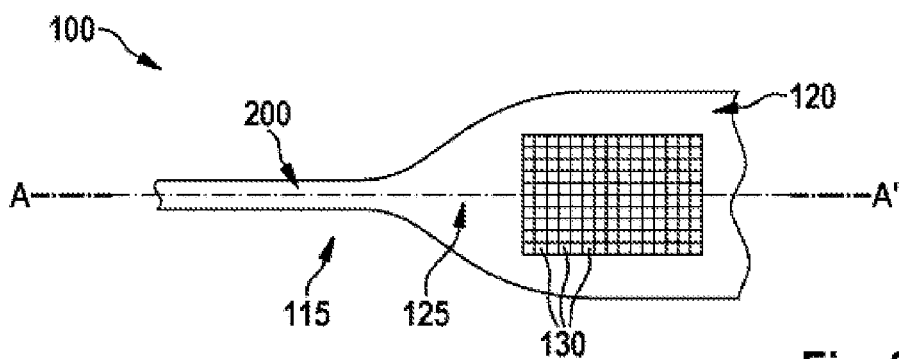
FIG. 2 shows a plan view of an analysis unit according to an illustrative embodiment of the present disclosure.

FIG. 2 shows a plan view of an analysis unit 100 according to an illustrative embodiment of the present disclosure. The bottom element 115 has a fluid channel 200, which opens into the bottom hollow 120 and is designed to convey the fluid onto the fluid-receiving surface 125. A section axis of the cross-sectional views shown in FIGS. 1a to 1c is indicated by a line AA'.

According to an illustrative embodiment of the present disclosure, a layered structure of the analysis unit 100 is composed of a first polymer substrate 105 with a through-hole 110, on the underside of which a deflectable polymer membrane 122 is mounted. In a plane parallel to this structure, a second polymer substrate 115 is arranged that carries an array of microcavities 130. By means of this arrangement, a microfluidic channel is formed as a fluid channel 200 that widens to a shallow chamber 120 in which the cavity array, also called the arrangement of microcavities 130, is located.

The polymer substrate 105 can also be designated as cover element 105, the through-hole 110 can also be designated as pressure channel 110 or through-opening, the second polymer substrate 115 can also be designated as bottom element 115, the deflectable polymer membrane 122 can also be designated as film 122 or membrane 122, and the shallow chamber 120 can also be designated as bottom hollow 120.

To allow the deflection of the polymer membrane 122 to take place in a controlled manner from left to right, it is particularly advantageous for an adhesive connection to be produced between the polymer membrane 122 and the polymer substrate 105, which adhesive connection is of such a nature that the connection comes undone initially in the area of the through-hole 110 and then slowly from left to right as a result of application of pressure. A connection of this kind that is reversible once can be provided, for example, by means of laser transmission welding.

According to a further illustrative embodiment, an array of cavities 130 is integrated in a layered polymer structure. The deflectable membrane 122 of the structure is used to fill the cavity array with a sample solution 135 to be tested, and it serves at the same time to cover the array and seal off the array cavities 130. The sample solution 135 can also be designated as fluid 135, sample volume 135 or sample 135. The cavity array is located in the same plane as the microfluidic channels 200. The membrane 122 is located over it.

The sample solution 135 is conveyed through a channel to an edge of the array and is stopped there. By deflection of the elastic membrane 122, the meniscus of the sample solution 135 is pushed across the cavity array in a controlled manner, whereupon the cavities 130 are filled by a capillary effect, as is shown in FIGS. 1b and 1c for example.

During the polymerase chain reaction, the membrane 122 remains deflected or lowered, as a result of which an array of cavities 130 is maintained for autonomous polymerase chain reactions.

In a further illustrative embodiment of the present disclosure, provision is made for the cavity array to be incorporated in lab-on-a-chip systems for the detection of nucleic acids by means of digital polymerase chain reaction. Such a system in the form of a microfluidic chip with an integrated cavity array allows sample preparation to be carried out together with downstream digital polymerase chain reaction on a polymer lab-on-a-chip multilayer system.

This affords the following advantages:

Together with sample preparation carried out in the same lab-on-a-chip system, a fully integrated diagnostic system is obtained that is able to detect DNA molecules at very low concentrations.

The flexible polymer membrane 122 of the multilayered structure permits controlled and automated filling of the cavities 130. In this way, operating errors are ruled out, and specially trained personnel are not needed to fill the cavities 130.

As a result of the sensitivity of the digital polymerase chain reaction, the field of use of lab-on-a-chip systems extends, for example, to noninvasive prenatal diagnostics, the detection of circulating tumor cells or cell-free tumor DNA, the detection of point mutations for personalized medicine, and the detection of very slight changes in gene expression.

The combination of sample preparation and digital polymerase chain reaction cuts down on manual operating steps and saves time.

A risk of contamination caused by carried polymerase chain reaction products can be reduced, since no purified products have to be manually transferred.

According to the prior art, DNA molecules can be detected in a two-step method involving end-product polymerase chain reaction and subsequent microarray analysis. By comparison, the proposed method offers a more rapid and simplified process.

Figure 3:
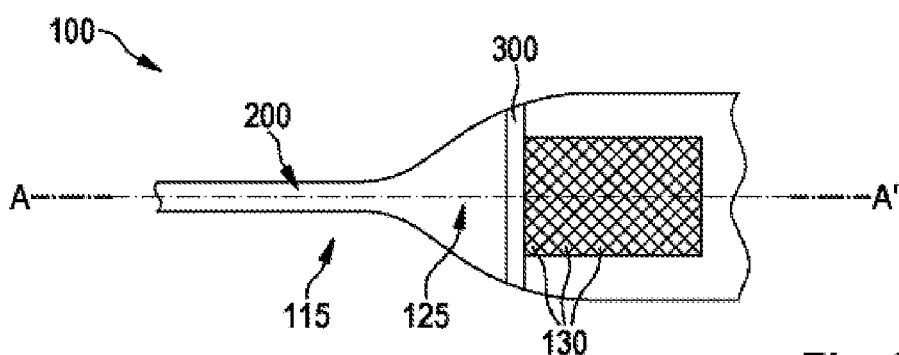
FIG. 3 shows a plan view of an analysis unit according to an illustrative embodiment of the present disclosure.

FIG. 3 shows a plan view of an analysis unit 100 according to an illustrative embodiment of the present disclosure. In contrast to FIG. 2, the analysis unit 100 shown in FIG. 3 has an optional separation element 300. The separation element 300 is arranged transversely with respect to the line AA'. According to this illustrative embodiment, the separation element 300 is designed as a groove in the bottom element 115, which groove extends across a full width of the bottom hollow 120. Moreover, the separation element 300 is arranged along an edge of the arrangement of microcavities 130 adjacent to the fluid-receiving surface 125.

The separation element 300 is designed to prevent a movement of the fluid from the fluid-receiving surface 125 into the microcavities 130 before the pressure has been applied at the through-opening.

Figure 4A:
FIGS. 4a and 4b show cross-sectional views of a bottom element with a separation element according to various illustrative embodiments of the present disclosure.
Figure 4B:
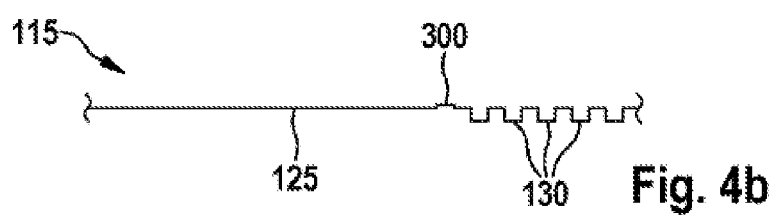

FIGS. 4a and 4b show cross-sectional views of a bottom element 115 with a separation element 300 according to various illustrative embodiments of the present disclosure.

FIG. 4a shows an illustrative embodiment in which the separation element 300, as shown in FIG. 3, is designed as a groove or trench.

FIG. 4b shows an illustrative embodiment in which, in contrast to FIGS. 3 and 4a, the separation element 300 is applied as a hydrophobic strip in an area of the fluid-receiving surface 125 adjacent to the microcavities 130.

According to various illustrative embodiments of the present disclosure, a left-hand edge of the cavity array has a feature as separation element 300 that brings about a defined stop of the sample volume. The feature can be realized, on the one hand, as a hydrophobic stop, as is shown in FIG. 4b, and, on the other hand, as a geometric stop, for example as a trench as shown in FIGS. 3 and 4a. By means of this configuration, it is possible to obtain a defined starting point for the distribution of the sample volume on the cavities 130.

Figure 5:
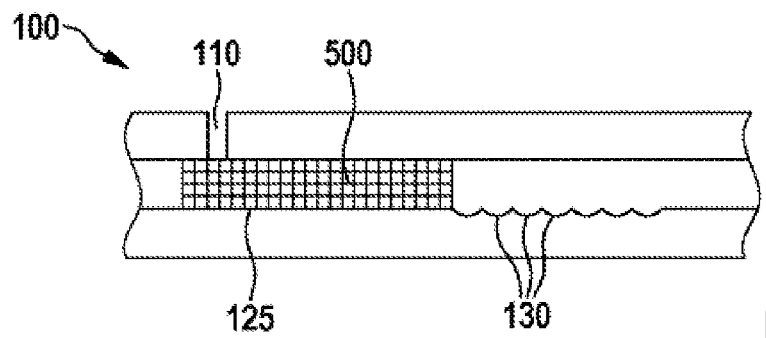
FIG. 5 shows a cross-sectional view of an analysis unit according to an illustrative embodiment of the present disclosure.

FIG. 5 shows a cross-sectional view of an analysis unit 100 according to an illustrative embodiment of the present disclosure. In contrast to FIGS. 1a to 4b described above, the fluid-receiving surface 125 shown in FIG. 5 is covered with a compressible fiber layer 500 from the area of the pressure channel 110 to the edge area of the fluid-receiving surface 125. The fiber layer 500 is designed to take up the fluid by suction and, when the pressure is applied on the pressure channel 110 by the film, to be compressed in such a way that the fluid is released again in the direction of the microcavities 130.

In a further embodiment, parts of the channel and of the shallow chamber contain an absorbent nonwoven as fiber layer 500, also called a sponge. This has the advantage that the sponge can take up a defined volume. By actuation of the polymer membrane, the volume located in the nonwoven can be introduced into the cavity array. In this way, in addition to a starting point being defined for the filling, a sample volume is at the same time also measured off.

Figure 6:
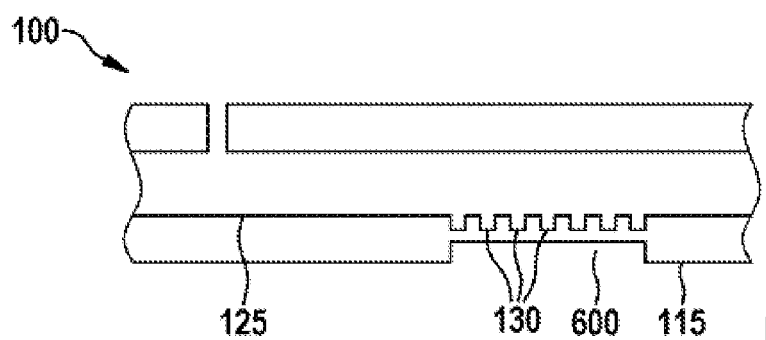
FIG. 6 shows a cross-sectional view of an analysis unit according to an illustrative embodiment of the present disclosure.

FIG. 6 shows a cross-sectional view of an analysis unit 100 according to an illustrative embodiment of the present disclosure. In contrast to the figures described above, the bottom element 115 shown in FIG. 6 has, in the area of the microcavities 130, a wall thickness which is smaller than the rest of the wall thickness of the bottom element 115. This permits easier access to the microcavities 130, for example in order to control the temperature of and/or analyze the fluid contained in the microcavities 130.

Optionally, a thinned area is formed as a recess 600 in the polymer substrate 115 underneath the cavity array. Firstly, this ensures that the thermal energy for performing the temperature-controlled polymerase chain reaction is introduced rapidly into the area of the cavity array. Secondly, an observation lens can be placed at a short physical distance from the cavity array, as a result of which the absorption fraction of the polymer substrate 115 is reduced.

Figure 7A:
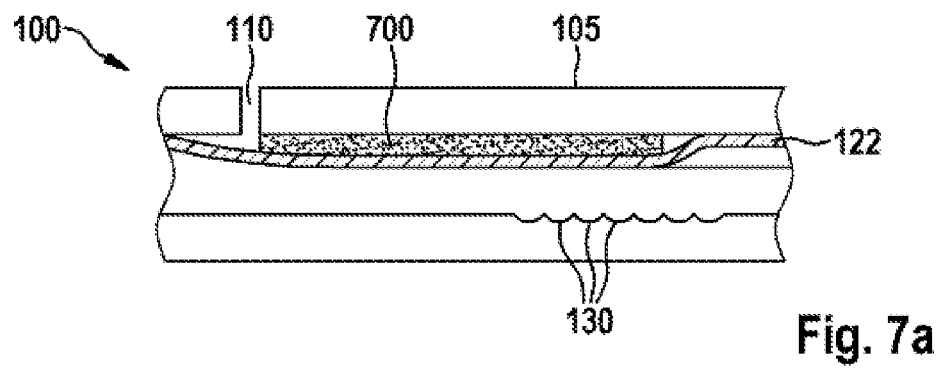
FIGS. 7a and 7b show cross-sectional views of an analysis unit according to an illustrative embodiment of the present disclosure.
Figure 7B:
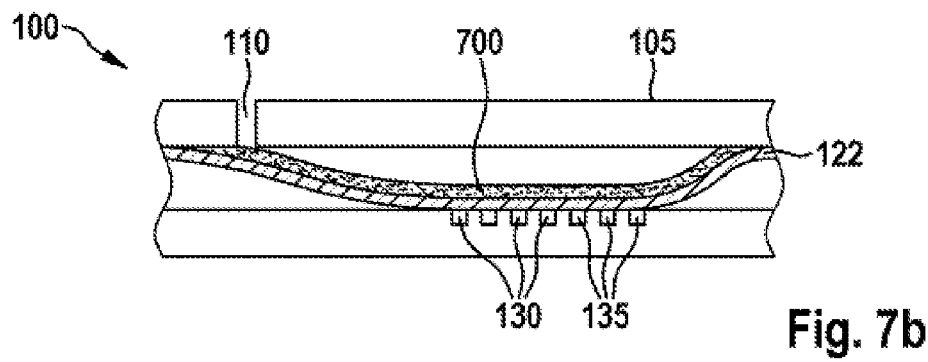

FIGS. 7a and 7b show cross-sectional views of an analysis unit 100 according to an illustrative embodiment of the present disclosure. In contrast to the figures described above, the film 122 shown in FIGS. 7a and 7b has an additional insulation layer 700. According to this illustrative embodiment, the insulation layer 700 is formed between the film 122 and the cover element 105. The insulation layer 700 here extends from the area of the through-opening 110 as far as an edge area of the arrangement of microcavities 130 directed away from the through-opening 110. The insulation layer 700 is designed to reduce a vapor permeability of the film 122.

FIG. 7a shows the film 122 in an undeflected state. FIG. 7b shows the film 122 in a deflected state, as has already been described with reference to FIGS. 1a to 1c.

A thin paraffin layer is additionally or alternatively formed as insulation layer 700 between the polymer substrate 105 and the polymer membrane 122. After the membrane 122 has undergone deflection and the paraffin layer has melted, the deflected membrane 122 is coated with the paraffin, as is shown in FIG. 7b. The vapor barrier thus obtained has the advantage that it does not require the use of liquid media and is activated automatically when the system, during operation, is exposed to temperature. This additionally has the advantage that, during production, the paraffin layer can be introduced as a solid, which means that liquid substances do not have to be dispensed.

According to a further illustrative embodiment, the surface of the polymer membrane 122 is coated such that the vapor permeability is reduced. All techniques known from the prior art can be used here. These are, for example, processes involving chemical vapor deposition (CVD) or physical vapor deposition (PVD).

In addition, the polymer membrane 122 can be realized as a multilayered composite. The vapor permeability can thus be reduced through the choice and composition of suitable materials. This embodiment has in particular the advantage that the content of the cavities 130 is sealed off even better, and the reliability of the system is thus increased.

Figure 8:
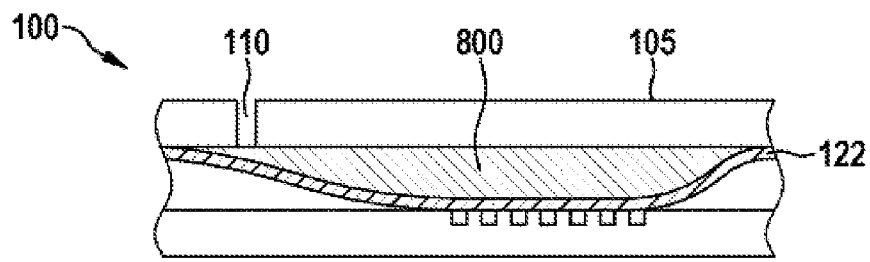
FIG. 8 shows a cross-sectional view of an analysis unit according to an illustrative embodiment of the present disclosure.

FIG. 8 shows a cross-sectional view of an analysis unit 100 according to an illustrative embodiment of the present disclosure. The film 122 is shown in a deflected state in FIG. 8. Here, the microcavities 130 are closed in a fluid-tight manner by the film 122. According to this illustrative embodiment, the analysis unit 100 is equipped with a means (not shown here) for introducing a pressure into the pressure channel 110. The means is designed to pump a liquid 800 through the pressure channel 110, such that the film 122 is bulged outward by the pressure of the liquid 800. The outward bulging of the film 122 causes the formation of a cavity between the film 122 and the cover element 105, which cavity is filled by the liquid 800.

By overlaying the deflected polymer membrane 122 with an externally delivered liquid medium 800, also called liquid 800, the evaporation of the sample volume 135 located in the cavities 130 can be additionally reduced. In this embodiment, a coating or a special layered structure of the polymer membrane 122 can be dispensed with.

The liquid medium 800 can be water, for example. In this case, with a suitable nature of the membrane 122, an exchange of water through the membrane 122 is possible. The cavities 130 do not run dry during a polymerase chain reaction, since loss of liquid is suppressed by diffusion of water through the membrane 122.

The liquid medium 800 can also be oil, photoresist, or an adhesive that can be activated by UV or heat. By overlaying the deflected polymer membrane 122 with the medium 800, a liquid diffusion barrier is obtained and loss of liquid is thereby suppressed.

Figure 9:
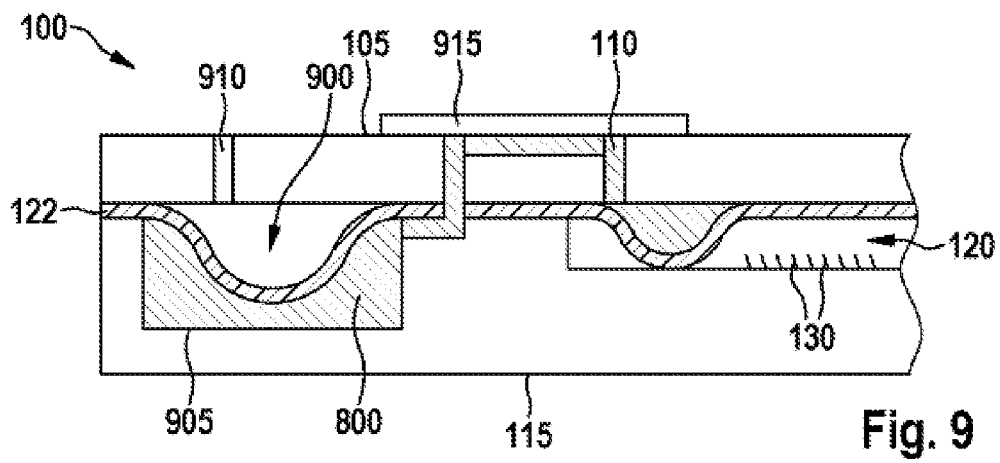
FIG. 9 shows a cross-sectional view of an analysis unit according to an illustrative embodiment of the present disclosure.

FIG. 9 shows a cross-sectional view of an analysis unit 100 according to an illustrative embodiment of the present disclosure. Here, the analysis unit 100 comprises a fluid container 900 as a further bottom hollow 905 in the bottom element 115. The film 122 is arranged between the further bottom hollow 905 and the cover element 105. The fluid container 900 is filled with a liquid and closed in a fluid-tight manner by the film 122. The cover element has a further pressure channel 910 in the area of the fluid container 900. According to this illustrative embodiment, the further pressure channel 910 is realized as a further through-opening in the cover element 105. Moreover, a connection channel 915 is formed in the cover element 105 in order to fluidically couple the fluid container 900 and the pressure channel 110.

As is shown in FIG. 9, a pressure can be applied to the film 122 through the further pressure channel 910, for example by means of a pump (not shown), such that the film 122 is deflected in the area of the fluid container 900. By means of the liquid, the pressure is diverted through the connection channel 915 and the pressure channel 110 to a part of the film 122 located in the area of the bottom hollow 120, such that the film 122 is also deflected in this area. The fluid is here forced into the microcavities 130.

An illustrative embodiment of the present disclosure provides for the integration of a reservoir as fluid container 900 for the liquid medium 800 described with reference to FIG. 8. By pressure being applied to this reservoir, the medium 800 is conveyed into the delivery channel 915, also called connection channel 915. The medium 800 then deflects the polymer membrane 122, as a result of which the cavity array is in turn closed in a vapor-tight manner.

This embodiment has the advantage that the medium does not have to be delivered from outside, thus making the process simpler to carry out. Since the medium 800 in this embodiment has no direct access to the outside world, there is the further advantage that the medium 800 cannot escape and, for example, contaminate an external control unit after completion of the process, when all the actuation pressures are removed.

Figure 10:
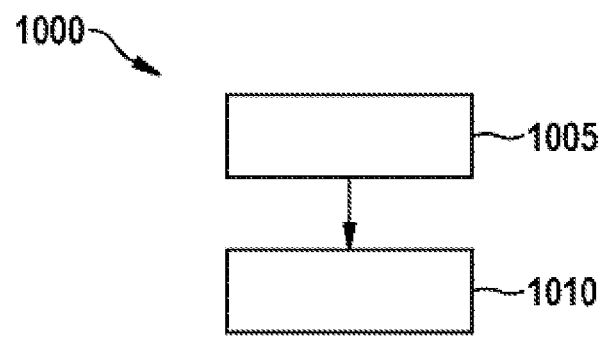
FIG. 10 shows a flow diagram of a method for operating an analysis unit according to an illustrative embodiment of the present disclosure.

FIG. 10 shows a flow diagram of a method 1000 for operating an analysis unit according to an illustrative embodiment of the present disclosure. In a step 1005, a fluid is first applied to the fluid-receiving surface. Then, in a step 1010, a pressure is introduced into the pressure channel in order to move the fluid from the fluid-receiving surface to the arrangement of microcavities.

According to an illustrative embodiment of the present disclosure, the sample volume 135 to be tested is conveyed into the channel 200 and part of the shallow chamber 120 and is stopped there. An overpressure is applied to the through-hole 110, as a result of which the polymer membrane 122 is deflected. The polymer membrane 122 thus descends from left to right. In this way, the sample volume 135 located beneath it is moved in the direction of the cavity array 130, as is shown in FIG. 1b. As soon as the membrane 122 has descended completely, all the cavities 130 have become filled with the sample 135 by capillary action (see FIGS. 1c, 7b and 8). The membrane 122 remains lowered during the conduct of the polymerase chain reaction, as a result of which the cavities 130 remain closed.

Figure 11:
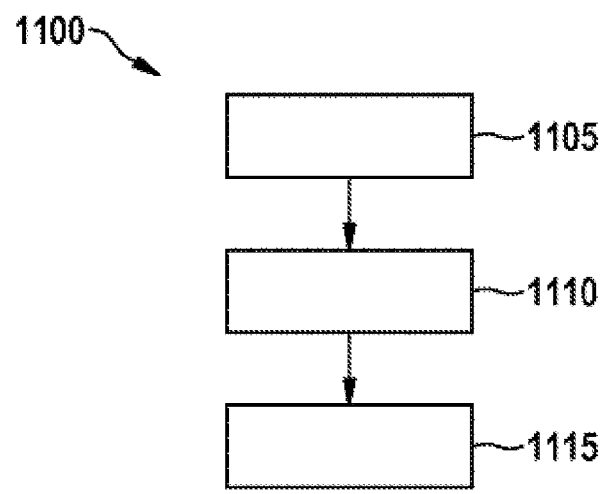
FIG. 11 shows a flow diagram of a method for producing an analysis unit according to an illustrative embodiment of the present disclosure.

FIG. 11 shows a flow diagram of a method 1100 for producing an analysis unit according to an illustrative embodiment of the present disclosure. In a step 1105, a bottom element with at least one bottom hollow, which has a fluid-receiving surface and an arrangement of microcavities, is made available, also a cover element with at least one pressure channel, which is designed to convey pressure into the area of the fluid-receiving surface, and a film. When the pressure is conveyed into the area of the fluid-receiving surface, the film is here designed to be deformed by the pressure in such a way that a fluid is moved from the fluid-receiving surface into the arrangement of microcavities.

In a further step 1110, the cover element, the bottom element and the film are joined together. They are joined together in such a way that the bottom hollow lies opposite the cover element and the film is arranged between the cover element and the bottom element in the area of the bottom hollow.

Finally, in a step 1115, at least one fluid channel is formed between the cover element and the bottom element, in order to convey the fluid to the fluid-receiving surface of the bottom hollow.

The necessary structures in the polymer substrates 105, 115 can be generated, for example, by milling, injection molding, hot-pressing or laser structuring. The cavity array can either be formed directly in the polymer or can be introduced into the polymer layered structure as an insert part, for example made of glass.

Examples of materials that can be used for the polymer substrate are thermoplastics such as polycarbonate (PC), polypropylene (PP), polyethylene (PE), polymethyl methacrylate (PMMA), cyclo-olefin polymer (COP) or cyclo-olefin copolymer (COC), and examples of materials that can be used for the polymer membrane are elastomer, thermoplastic elastomer based on urethane (TPU), styrene block copolymers (TPS), thermoplastics, hot-bonding films or sealing films for microtiter plates.

As examples of the dimensions in the illustrative embodiments, the thickness of the polymer substrate can be 0.5 to 5 mm, the channel diameter in the polymer substrates can be 10 μm to 3 mm, the thickness of the polymer membrane can be 5 to 500 μm, and the lateral dimensions of the entire illustrative embodiment can be 10×10 mm$^2$ to 200×200 mm$^2$.

The volume of the cavities of the array can be 1 fl to 100 μl.

The number of cavities can reach $10^1$ to $10^9$, for example.

The illustrative embodiments that have been described and that are shown in the figures have been chosen only as examples. Different illustrative embodiments can be combined with each other either in full or in terms of individual features. It is also possible for an illustrative embodiment to be supplemented by features of another illustrative embodiment.

Moreover, method steps according to the disclosure can be repeated and can be carried out in an order different than that described.

If an illustrative embodiment comprises an "and/or" link between a first feature and a second feature, this should be read as meaning that the illustrative embodiment, in one form, has both the first feature and also the second feature and, in another form, has either just the first feature or just the second feature.

The invention claimed is:

1. An analysis unit for performing a polymerase chain reaction, comprising:
    a cover element;
    a bottom element, including:
        at least one bottom hollow positioned facing toward the cover element the at least one bottom hollow having a fluid-receiving surface and an arrangement of microcavities; and
        at least one microfluidic channel arranged facing toward the cover element and configured to convey a fluid onto the fluid-receiving surface of the bottom hollow without filling the microcavities;
    a film positioned between the cover element and the bottom element in an area of the bottom hollow, and
    at least one pressure channel arranged in the cover element and configured to convey a pressure toward the area of the bottom hollow,
    wherein the film is configured to deform in response to the pressure such that the fluid is moved from the fluid-receiving surface into the arrangement of microcavities.

2. The analysis unit as claimed in claim 1, wherein:
    the at least one pressure channel is defined by a through-opening in the cover element,
    the bottom hollow is positioned such that the fluid-receiving surface lies opposite the through-opening, and
    the arrangement of microcavities is laterally offset with respect to the through-opening.

3. The analysis unit as claimed in claim 1, wherein the film is secured releasably on the cover element at least in at least one of the area of the fluid-receiving surface and an area of the arrangement of microcavities.

4. The analysis unit as claimed in claim 1, wherein the film is configured to deform in response to the pressure such that the arrangement of microcavities is closed in a fluid-tight manner.

5. The analysis unit as claimed in claim 1, further comprising:
    a separation element arranged between the arrangement of microcavities and the fluid-receiving surface and configured to prevent a movement of the fluid from the fluid-receiving surface into the arrangement of microcavities in an absence of pressure conveyed into the area of the fluid-receiving surface.

6. The analysis unit as claimed in claim 1, further comprising a compressible fiber layer that at least partially covers the fluid-receiving surface, and that is configured to at least one of take up and release the fluid.

7. The analysis unit as claimed in claim 1, wherein the bottom element has a predetermined maximum thickness in an area of the arrangement of microcavities.

8. The analysis unit as claimed in claim 1, wherein the film, at least in an area of the arrangement of microcavities, at least one of (i) has an insulation layer and (ii) includes a multi-layer composite configured to reduce a vapor permeability of the film.

9. The analysis unit as claimed in claim 8, wherein the insulation layer is formed on a side of the film facing toward the cover element.

10. The analysis unit as claimed in claim 1, further comprising:
    a further bottom hollow in the bottom element defined by a fluid container;
    at least one further pressure channel arranged in the cover element and configured to convey a further pressure into the fluid container; and
    at least one connection channel arranged in the cover element and configured to couple the fluid container and the pressure channel fluidically,
    wherein the fluid container is configured to convey the further pressure through the connection channel and the pressure channel into the area of the fluid-receiving surface.

11. The analysis unit as claimed in claim 10, further comprising:
    a mechanism configured to introduce pressure into at least one of the pressure channel and the further pressure channel.

12. A method for operating an analysis unit comprising:
    applying a fluid via a microfluidic channel to a fluid-receiving surface of a bottom hollow defined by a bottom element, the bottom element further defining an arrangement of microcavities and the microfluidic channel, the bottom hollow and the microfluidic channel arranged facing toward a cover element, and the microfluidic channel configured to convey the fluid onto the fluid-receiving surface without filling the microcavities; and
    introducing a pressure into a pressure channel arranged in the cover element and configured to convey pressure toward an area of the bottom hollow, the pressure configured to deform a film positioned between the cover element and the bottom element in the area of the bottom hollow, the film configured such that deformation in response to the pressure causes the fluid to move from the fluid-receiving surface into the arrangement of microcavities.

13. A method for producing an analysis unit comprising:
    providing a bottom element, a cover element and a film, the bottom element including at least one bottom hollow and at least one microfluidic channel, the at least one bottom hollow having a fluid-receiving surface and an arrangement of microcavities, the cover element including at least one pressure channel, and the film configured to deform in response to pressure; and
    joining together the cover element, the bottom element and the film such that the bottom hollow and the at least one microfluidic channel face toward the cover element, such that the at least one microfluidic channel is configured to convey a fluid onto the fluid-receiving surface of the bottom hollow without filling the microcavities, such that the pressure channel is configured to convey a pressure toward an area of the bottom hollow, such that the film is positioned between the cover element and the bottom element in the area of the bottom hollow, and such that pressure conveyed toward the area of the bottom hollow causes the film to deform and move the fluid from the fluid receiving surface into the arrangement of microcavities.

* * * * *